(12) United States Patent
Sugiyama et al.

(10) Patent No.: US 6,946,455 B2
(45) Date of Patent: Sep. 20, 2005

(54) INTERSTRAND CROSSLINKING AGENTS FOR DNA AND COMPOUNDS THEREFOR

(75) Inventors: Hiroshi Sugiyama, Tokyo (JP); Toshikazu Bando, Tokyo (JP); Hirokazu Iida, Tokyo (JP); Isao Saito, Kyoto (JP)

(73) Assignee: Japan Science and Technology Corporation, Saitama (JP)

( * ) Notice: Subject to any disclaimer, the term of this patent is extended or adjusted under 35 U.S.C. 154(b) by 307 days.

(21) Appl. No.: 10/030,678

(22) PCT Filed: May 1, 2001

(86) PCT No.: PCT/JP01/03756
§ 371 (c)(1),
(2), (4) Date: May 23, 2002

(87) PCT Pub. No.: WO01/85733
PCT Pub. Date: Nov. 15, 2001

(65) Prior Publication Data
US 2004/0086851 A1 May 6, 2004

(30) Foreign Application Priority Data
May 12, 2000 (JP) ........................................ 2000-140361

(51) Int. Cl.[7] ........................ A61K 31/33; A61K 31/44; A01N 43/90; A01N 43/38; C07D 209/56
(52) U.S. Cl. .................... 514/183; 514/259.1; 514/283; 514/410; 548/427; 548/428; 548/433
(58) Field of Search .............................. 514/183, 259.1, 514/283, 410; 548/427, 428, 433

(56) References Cited

FOREIGN PATENT DOCUMENTS

| EP | 1 083 177 | 3/2001 |
|---|---|---|
| JP | 11-500427 | 1/1999 |
| JP | 2000-511893 | 9/2000 |
| JP | 2000-281679 | 10/2000 |
| WO | WO 96/23497 | 8/1996 |
| WO | WO 97/44000 | 11/1997 |
| WO | WO 00/12523 | 3/2000 |
| WO | WO 00/15641 | 3/2000 |
| WO | WO 01/36677 A1 | 5/2001 |

OTHER PUBLICATIONS

Lee et al. J. Am. Chem. Soc. 1997, 119, 3434–3442.*
T. Bando et al., *Journal of the American Chemical Society*, 123(21):5158–5159 (2001).

* cited by examiner

*Primary Examiner*—Jezia Riley
(74) *Attorney, Agent, or Firm*—Peter F. Corless; Christine C. O'Day; Edwards & Angell, LLP

(57) ABSTRACT

Compounds represented by the general formula (I): which two DNA strands can be interstrand-crossliked:

$$A\text{-}L\text{-}B\text{-}X\text{-}B\text{-}L\text{-}A \qquad (I)$$

wherein B represents a chemical structure capable of recognizing the nucleotide sequence of DNA; A represents a chemical structure capable of binding to one of the bases of DNA; L represents a linker by which the chemical structures of A and B can be linked to each other; X represents a spacer by which the A-L-B components can be linked to each other. A method of interstrand-crosslinking DNA by using these compounds; and medicinal compositions containing interstarand-crosslinking agents of DNA.

12 Claims, 5 Drawing Sheets

SEQUENCE LISTING

<160> NUMBER OF SEQ ID NOS: 11

<210> SEQ ID NO 1
<211> LENGTH: 5
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent

<400> SEQUENCE: 1 cgacg                                                                    5

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent

<400> SEQUENCE: 2
ttacagtggc tgccagca                                                     18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent

<400> SEQUENCE: 3
ttatgctggc agccactg                                                     18

<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent

<400> SEQUENCE: 4
ttacagtggc tgcc                                                         14

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent

<400> SEQUENCE: 5
ttacagtggc gccagca                                                      17

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent

<400> SEQUENCE: 6
ttacagtggc tgccagca                                                    18

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent

<400> SEQUENCE: 7
ttacagtggc ttgccagca                                                   19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent
<220> FEATURE:
<221> NAME/KEY: misc_feature
<222> LOCATION: (11)..(13)
<223> OTHER INFORMATION: This region may encompass 0 to 3 residues

<400> SEQUENCE: 8
ttacagtggc tttgccagca                                                  20

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent

<400> SEQUENCE: 9
ttacagtggc tgcc                                                        14

<210> SEQ ID NO 10
<211> LENGTH: 9
<212> TYPE: DNA
<213> ORGANISM: Artificial Sequence
<220> FEATURE:
<223> OTHER INFORMATION: Description of Artificial Sequence: Synthetic
      nucleic acid interstrand-crosslinking agent

<400> SEQUENCE: 10 tggctgcca                                                               9

```
<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:  Synthetic
      nucleic acid interstrand-crosslinking agent
<220> FEATURE:
<221> NAME/KEY: misc_feature
<222> LOCATION: (8)..(10)
<223> OTHER INFORMATION: This region may encompass 0 to 3 residues

<400> SEQUENCE: 11
tgctggcaaa gccactg                                                17
```

INTERSTRAND CROSSLINKING AGENTS FOR DNA AND COMPOUNDS THEREFOR

TECHNICAL FIELD

The present invention relates to a compound capable of simultaneously alkylating and excising double-stranded DNA, which can be prepared by chemical synthesis. Also the present invention relates to a method for alkylating DNA with such compound and a method for excising double-stranded DNA. Further also the present invention relates to a pharmaceutical composition comprising such compound.

BACKGROUND OF THE INVENTION

The Human Genome Project is now on the way of elucidation of the nucleotide sequences of all the genes of our humans in a coming few years, and the genes are serving as "the design scheme of life". It is known that the design scheme if it happens to have any damage or an acquired damage may cause diseases or aging. The progress of the Human Genome Project has enabled the understanding of many diseases including cancer at DNA level. Thus, medicine principally including diagnostics and prophylaxis will wholly make a possible innovative change. Further, the development of therapeutic treatments based on the understanding of these diseases at DNA level, namely pharmaceutical products targeting the pathologic genes and the products of the genes, has been strongly desired. However, research works linking fundamental researches to clinical researches have just started.

Cancer has also been investigated at DNA level, but anti-cancer agents for current use are mostly composed of antibiotics selected through screening, not microbial products generated by microorganisms so as to kill cancer cells. Anti-cancer agents based on the findings in the molecular biology of cancer scarcely exist. If extracellular free control of the expression of a specific intracellular gene can be achieved, the control will serve for an ultimate therapeutic therapy of cancer at gene level.

A chemical modification of DNA carrying genetic information damages the genetic information composing the fundamental base for the sustainment of viability, leading to the induction of cellular mutation and death. Additionally, it has been known that a modification via covalent bonding to the DNA in normal cell is a cause of oncogenes is, while interaction with the DNA in cancer cell can be utilized for anti-cancer agent.

The interstrand-crosslinking reaction as shown by the following formula:

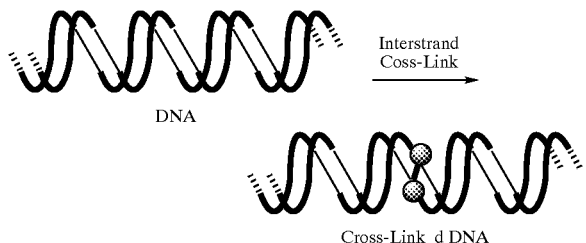

, which works for crosslinking the double strands of DNA, inhibits DNA replication as confirmed in various systems. It has been known that the interstrand-crosslinking reaction has far more potent actions on living organisms, compared with single-strand alkylation [S. R. Rajski and R. M. Williams, Chem. Rev., 2723–2795 (1998)].

For example, phage inactivation only requires the occurrence of interstrand-crosslinking at 1.3 equivalents on average, but the alkylation of simple single strand requires 280 equivalents of alkylation agents [P. D. Lawley, J. H. Lethbridge, P. A. Edwards, K. V. Shooter, J. Mol. Biol., 39, 181 (1969)].

Mitomycin and carzinophyllin A have been known as anti-cancer antibiotics inducing typical interstrand-crosslinking reaction. Further, numerous compounds with DNA interstrand-crosslinking actions, typically including bizelecin, have been reported so far. As representative compounds reported by far to induce DNA interstrand-crosslinking reaction, the following mitomycin, carzinophyllin A and nitrogen mustard have been known.

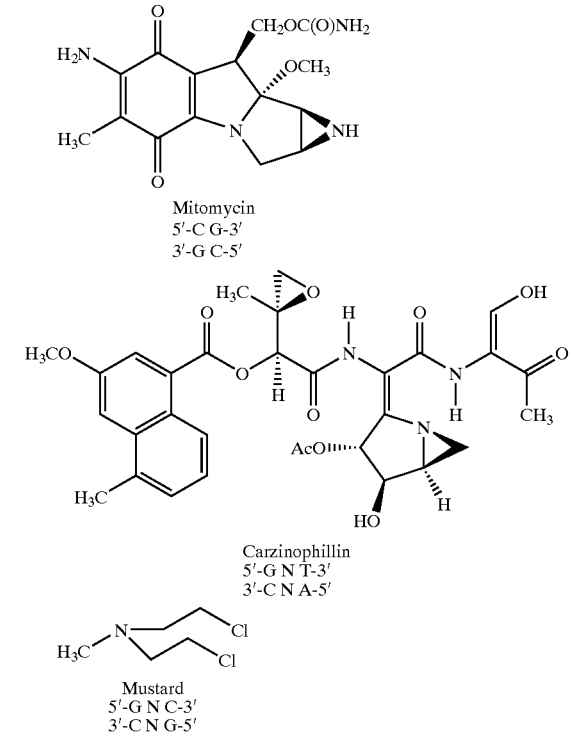

Such mitomycin, nitrogen mustard (mechlorethamine) and the like are currently used as efficacious anti-cancer agents in clinical practice.

The nucleotide sequence specificities of various interstrand-crosslinking agents have been examined in detail up to now. (a) S. -J. Lee, F. C. Seaman, D. Sun, H. Xiong, R. C. Kelley, L. H. Hurley, J. Am. Chem. Soc., 119, 3434–3442 (1997); b) J. T. Millard, R. J. Spencer, P. B. Hopkins, Biochemistry, 37, 5211–5219 (1998); c) T. Fujiwara, I. Saito, H. Sugiyama, Tetrahedron Lett., 40, 315–318 (1999)). However, no correlation between the anti-cancer profiles of these compounds and the nucleotide sequence selectivities of the interstrand-crosslinking agents has yet been established. Further, no success has been made in the molecular designing of an interstrand-crosslinking compound directed for an arbitrary nucleotide sequence. Still further, the DNA interstrand-crosslinking agents synthetically prepared previously are generally at very low reaction efficiencies. For example, interstrand crosslinked products are prepared by the mustard with a known crosslinking potency of the 5'-GNC nucleotide sequence in DNA, at a yield as low as only several percents of the DNA used (Y.-H. Fan and B. Gold, J. Am. Chem. Soc., 121, 11942–11946 (1999)).

Thus, very importantly, an efficient DNA interstrand-crosslinking agent will be developed.

DISCLOSURE OF THE INVENTION

The present invention provides an efficient interstrand-crosslinking DNA agent, a compound therefor, and a pharmaceutical composition using the same.

BEST MODE FOR CARRYING OUT THE INVENTION

Figure 1:
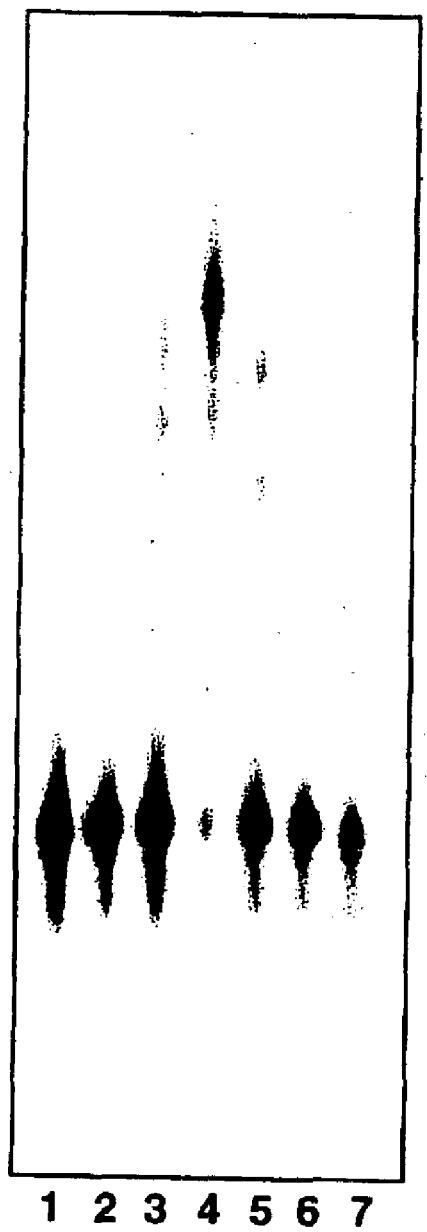
FIG. 1 is a photograph as a drawing substitute and shows the experimental results of the analysis of the interstrand-crosslinking of the inventive compound using polyacrylamide gel electrophoresis.

The present inventors have made analyses of the DNA alkylation potency of the hybrid molecule (1) represented by the following formula (1):

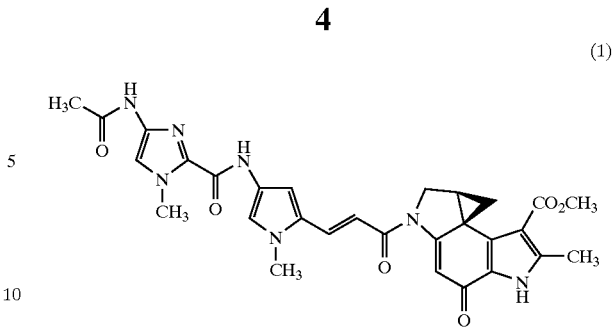

(1)

, which is prepared by introducing vinyl group in between the pyrrole-imidazole diamide moiety having DNA nucleotide sequence-recognizing potency and the duocarmycin segment. The hybrid molecule (1) forms a homodimer, which performs selective double alkylation of a specific nucleotide sequence in DNA, as depicted by the following formula.

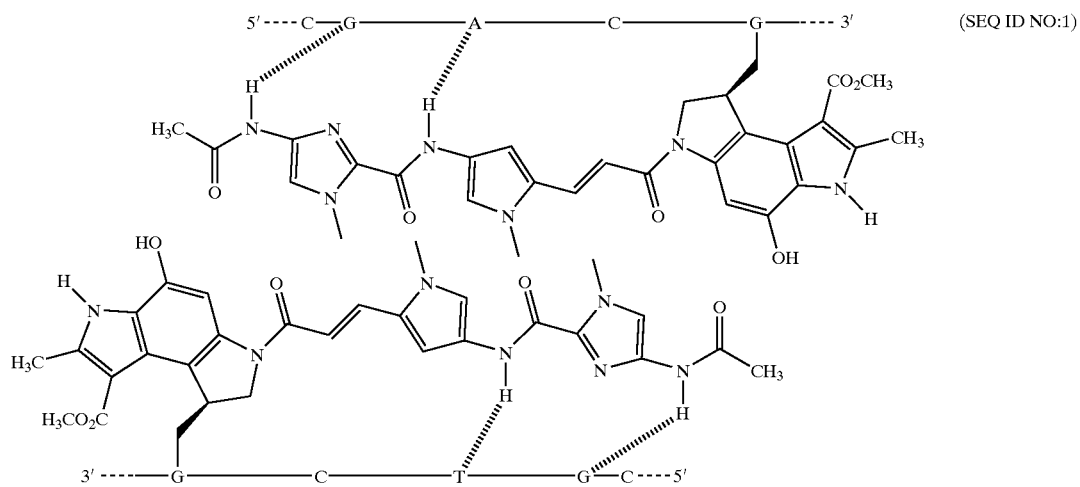

(SEQ ID NO:1)

The compound is a molecule with the structure: A-L-B-R type where vinyl group is used as linker L (in the formula, B represents a chemical structure capable of recognizing DNA nucleotide sequence; A represents a chemical structure capable of binding to one of the bases in DNA; L represents a linker capable of linking the chemical structures of A and B together; and R presents terminal group such as alkyl group (see Japanese Patent Application No. 83591/1999).

Therefore, the present inventors have made investigations on the basis of this type of molecules. The inventors have found that compounds prepared by linking the type of a molecule with spacers of different lengths are compounds with efficient DNA interstrand-crosslinking potencies.

The invention relates to a compound capable of interstrand-crosslinking the double strands of DNA, as represented by the general formula (I):

A-L-B-X-B-L-A (I)

(wherein, B represents a chemical structure capable of recognizing the nucleotide sequence of DNA; A represents a chemical structure capable of binding to one of the bases of DNA; L represents a linker by which the chemical structures of A and B can be linked to each other; X represents a spacer by which the A-L-B components can be linked each other.)

Further, the invention relates to a method for interstrand-crosslinking DNA, using the compound; the interstrand-crosslinking DNA agent; and a pharmaceutical composition containing the same.

For the purpose of developing a compound with interstrand-crosslinking potency, the inventors synthetically prepared the compounds (7a–d) prepared by binding the hybrid molecule (1) together via spacers of different lengths:

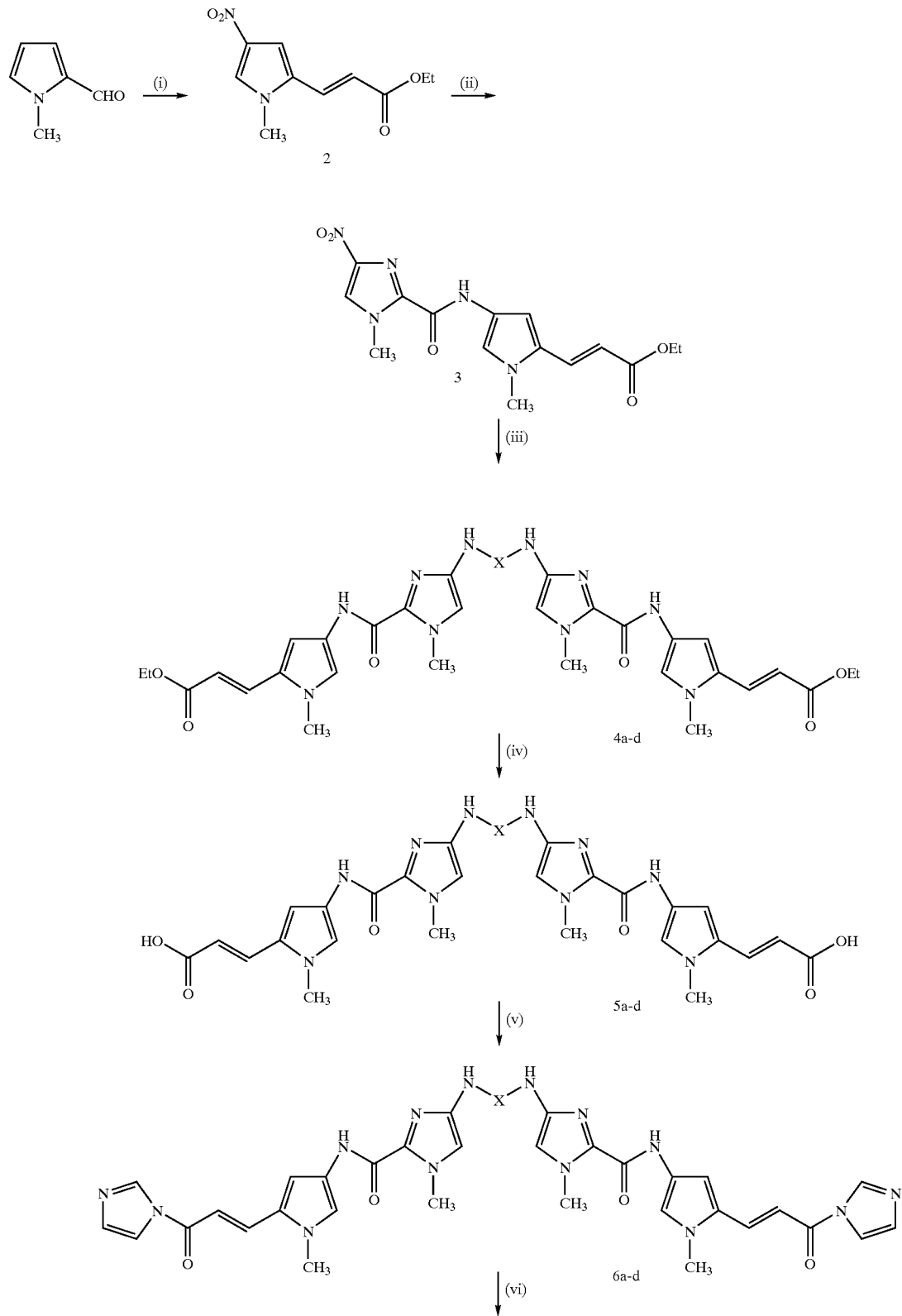

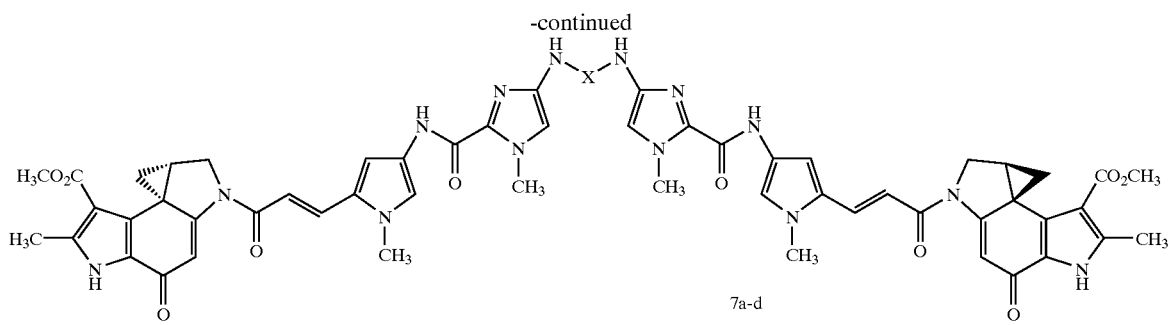

7a-d wherein, X represents the followings:

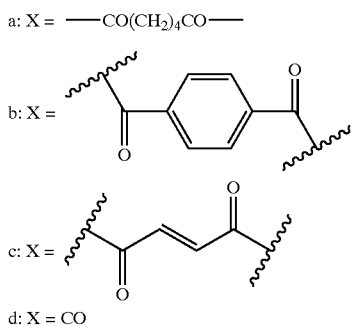

The synthesis of the compounds (7a–d) was done by condensing activated carbonyl compounds constituting spacer respectively corresponding to diamide derivatives (3) with the diamide derivatives.

First, N-methyl-2-pyrrolaldehyde is nitrated with nitric acid or the like, which is then prepared into ester (2), using a Wittig-type reagent such as $(EtO)_2P(O)CHCO_2Et$. The resulting ester (2) is reduced with a metal hydride such as $NaBH_4$ into an amino material, which reacts with 1-methyl-3-nitro-5-trichloroacetylimidazole to prepare an imidazole-pyrrole compound (3). The compound is then reduced by the same method as described above so as to reduce the nitro group into amino group, which reacts with an acid halogenide or carbonyldiimidazole (CDI), depending on the objective compound, to prepare dimer compounds (4a–d). Subsequently, the ester groups at both the ends are hydrolyzed to prepare free carboxylic acids (5a–d), which are then prepared into active amides (6a–d), using CDI. The resulting amides react with the segment A of an antibiotic DU86, to prepare the objective compounds (7a–d).

The synthetic process is a process with such great versatility that the process is applicable to the synthesis of the same type of symmetric dimer. The compound of the invention can be produced according to the method.

Using the compounds (7a–d) as examples, the invention will be described more specifically.

The interstrand-crosslinking reaction of double-stranded DNA using such compound was experimentally examined, using the following DNA pair of 18 bases and 15 bases.

5'-TTACAGTGGCTGCCAGCA-3'(SEQ ID NO: 2)    (ODN-18)

3'-GTCACCGACGGTCGT-5'    (ODN-15)

The 5'-terminus of ODN-18 is labeled with Texas Red (TXRed), which is therefore referred to as TXR-18.

At the experiments, a compound represented by the following formula:

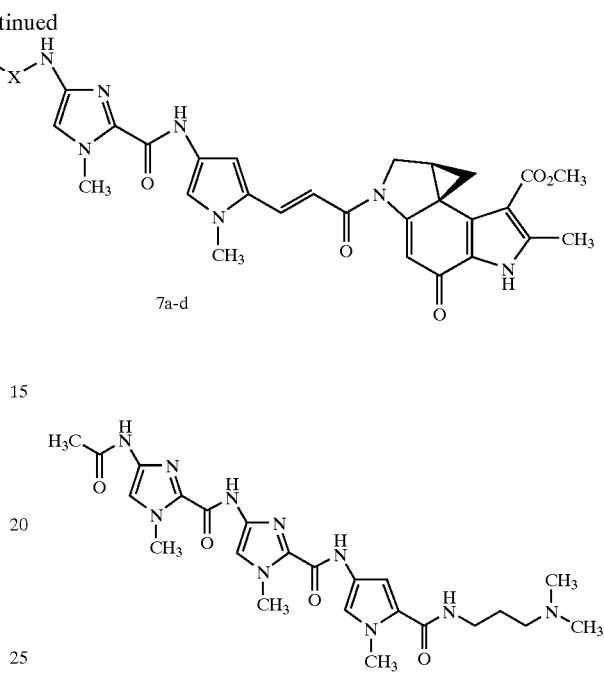

(the compound is referred to as ImImPy in the present specification) was used as an auxiliary reagent. In the present specification, the ImImPy was used as the "substance with a chemical structure capable of recognizing the nucleotide sequence of DNA".

Adding the inventive compounds (7a–d) and if necessary ImImPy to the DNA, the interstrand-crosslinking reaction of the DNA oligomers with the compounds (7a–d) was analyzed by polyacrylamide gel electrophoresis.

The results are shown in FIG. 1, a photograph as a drawing substitute. In FIG. 1, lane 1 represents the case of only TXR-18 (3 μM) and ODN-15 (6 μM), lane 2 represents the case of ImImPy (100 μM) added to TXR-18 (3 μM) and ODN-15 (6 μM), lane 3 represents the case of the compound (7a) (50 μM) added to TXR-18 (3 μM) and ODN-15 (6 μM), lane 4 represents the case of the compound (7a) (50 μM) and ImImPy (100 μM) added to TXR-18 (3 μM) and ODN-15 (6 μM), lane 5 represents the case of the compound (7b) (50 μM) and ImImPy (100 μM) added to TXR-18 (3 μM) and ODN-15 (6 μM), lane 6 represents the case of the compound (7c) (50 μM) and ImImPy (100 μM) added to TXR-18 (3 μM) and ODN-15 (6 μM), and lane 7 represents the case of the compound (7d) (50 μM) and ImImPy (100 μM) added to TXR-18 (3 μM) and ODN-15 (6 μM).

Consequently, almost no reaction with the compound (7a) alone could be observed (Lane 3), but in the presence of ImImPy, the starting raw material DNA fragment TXR-18 was modified into a band with a low electrophoretic mobility (Lane 4). The compounds (7b–d) with other spacers, even singly or in combination with ImImPy, could hardly generate such a band with a low electrophoretic mobility, as observed in the Lane 4 (Lanes 5, 6 and 7). These findings indicate that the compound (7a) used in combination with ImImPy induced an extremely specific reaction with the DNA oligomer TXR-18.

So as to confirm that the band observed then was derived from an interstrand-crosslinked product, subsequently, an experiment was done, using two sets of DNA pairs, comprising oligomer with independently labeled upper strand (TXR-18) and lower strand (TXR-18R). More specifically, the pair of TXR-18 and ODN-15 and the pair of ODN-15R and TXR-18R described below was used.

5'-CAGTGGCTGCCAGCA-3' (ODN-15R)

3'-GTCACCGACGGTCGTATT-5'(SEQ ID NO: 3) (ODN-18R)

The TXR-18R used is the nucleotide ODN-18R with the 5'-terminus labeled with Texas Red (TXRed).

At the experiment, additionally, the following nucleotides TXR-14 and TXR-14R shown below were used as standard products.

5'-TTACAGTGGCTGCC-3'(SEQ ID NO: 4) (ODN-14)

3'-CCGACGGTCGTATT-5' (ODN-14R)

These nucleotide sequences were all designed to be identical to the 5'-terminal nucleotide sequences of ODN-18 or ODN-18R. TXR-14 is the nucleotide ODN-14 with the 5' terminus labeled with Texas Red (TXRed). Similarly, TXR-14R is the nucleotide ODN-14R with the 5'-terminus labeled with Texas Red (TXRed).

Figure 2:
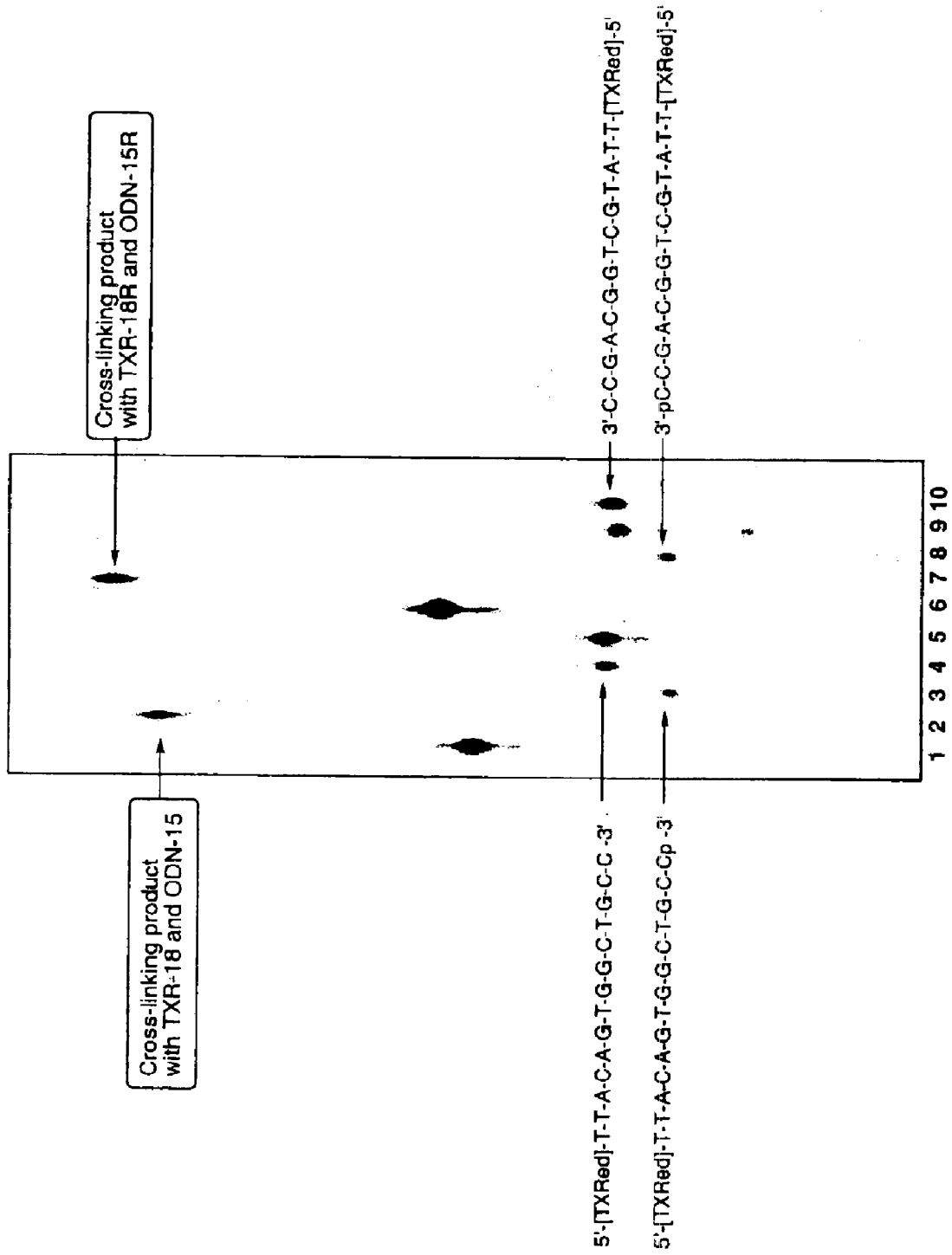
FIG. 2 is a photograph as a drawing substitute and shows the experimental results of the analysis of the interstrand-crosslinking reaction of the inventive compound using two sets of DNA pairs (SEQ ID NOS: 4 and 9).

The results are shown in a photo picture as a drawing substitute in FIG. 2. In FIG. 2, lane 1 represents the case of only TXR-18 (3 μM) and ODN-15 (6 μM), lane 2 represents the case of compound (7a) (50 μM) and ImImPy (100 μM) added to TXR-18 (3 μM) and ODN-15 (6 μM), lane 3 represents the same case as in Lane 2, additionally with a heating treatment at 90° C. for 20 minutes and piperidine treatment at 90° C. for 20 minutes, lane 4 represents the same case as in Lane 3, additionally with a treatment with an alkaline dephosphorylation enzyme at 37° C. for 2 hours, lane 5 represents the standard product TXR-14, lane 6 represents the case of only TXR-18R (3μM) and ODN-15R (6 μM), lane 7 represents the case of the compound (7a) (50 μ) and ImImPy (100 μM) added to TXR-18R (3 μM) and ODN-15R (6 μM), lane 8 represents the same case as in Lane 7, additionally with a heating treatment at 90° C. for 20 minutes and piperidine treatment at 90° C. for 20 minutes, lane 9 represents the same case as in Lane 8, additionally with a treatment with an alkaline dephosphorylation enzyme at 37° C. for 2 hours, and lane 10 represents the standard product TXR-14R.

Novel products were confirmed at the experiments (Lanes 2 and 7), which might possibly be interstrand-crosslinked products. Meanwhile, excised fragments were recovered by the heating treatment and the piperidine treatment (Lanes 3 and 8). Further AP (alkaline phosphatase) treatment of the fragments reduced the electrophoretic mobilities (Lanes 4 and 9). The products were identified as the same products as the separately synthesized standard products, by polyacrylamide gel electrophoresis (Lanes 5 and 10).

The experimental results reveal that the DNA oligomers were sequence-selectively alkylated at the two adenine sites by the compound (7a) and ImImPy. Taking account of the finding that such large change of the electrophoretic rate was observed through the reaction, it was verified that the interstrand-crosslinking reaction of DNA progressed almost quantitatively.

Figure 3:
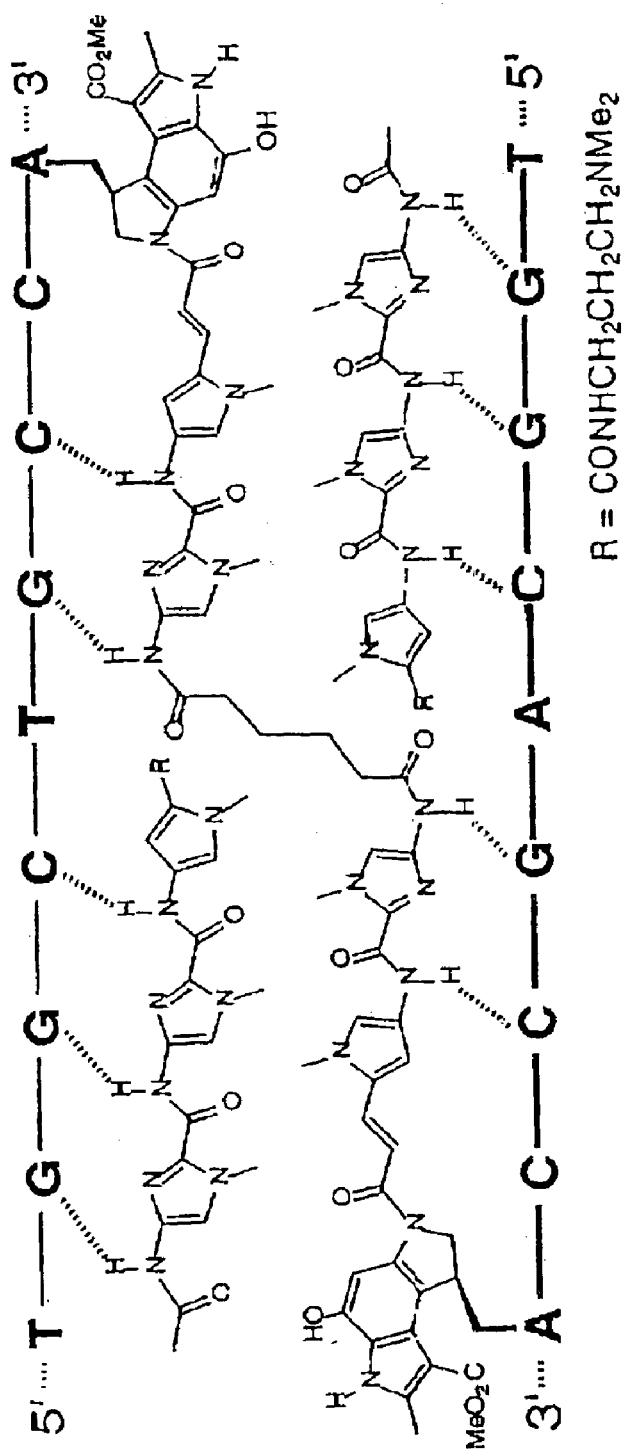
FIG. 3 shows the chemical structure of the resulting interstrand crosslinked product, using the inventive compound (7a) and ImImPy.

These results demonstrate that pyrrole-imidazole polyamide CPI conjugate (7a) can efficiently perform DNA interstrand-crosslinking only in the presence of triamide, according to the rule of the nucleotide sequence recognition by pyrrole-imidazole. See (a) P. B. Dervan, et al., Nature, 282, 111–115 (1998); b) T. Fujiwara, Z.-F. Tao, Y. Ozeki, I. Saito, A. H.-J. Wang, M. Lee, H. Sugiyama, J. Am. Chem. Soc., 121, 7706–7707(1999). The structure of the interstrand-crosslinked product generated by the compound (7a) and ImImPy is shown in FIG. 3.

The nucleotide sequence specificity of the interstrand-crosslinking was then examined.

So as to examine the sequence specificity of the interstrand-crosslinking via the compound (7a) and ImImPy, it was examined whether the crosslinking reaction of the compound (7a) might be modified in the presence of ImImPy and other three types of triamides. The structures of the triamides used at the experiments are shown below.

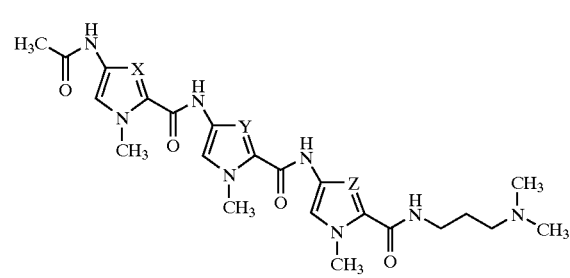

ImImPy: X = N, Y = N, Z = CH
ImImIm: X = N, Y = N, Z = N
ImPyPy: X = N, Y = CH, Z = CH
PyImPy: X = CH, Y = N, Z = CH

Wherein, ImImPy represents the structure where X=N, Y=N, and Z=CH;

ImImIm represents the structure where X=N, Y=N, and Z=N;

ImPyPy represents the structure where X=N, Y=CH, and Z=CH;

PyImPy represents the structure where X=CH, Y=N, and Z=CH.

Figure 4:
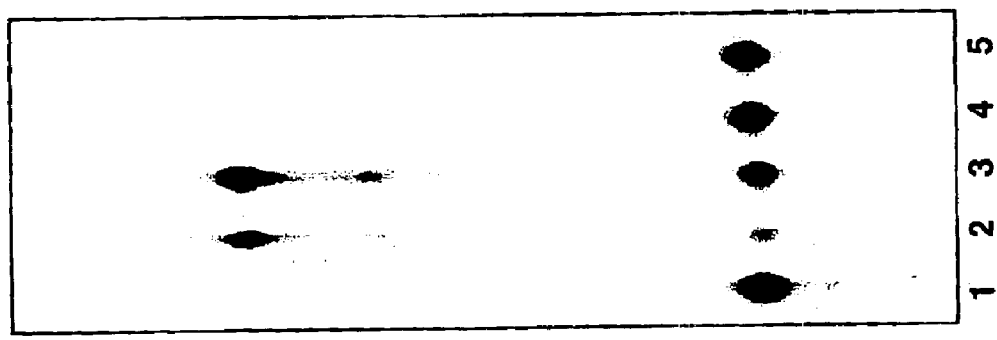
FIG. 4 is a photograph as a drawing substitute and shows the experimental results of the analysis of the interstrand-crosslinking reaction of the inventive compound, using various triamides in combination.

The results are shown in a photograph as a drawing substitute in FIG. 4. In FIG. 4, lane 1 represents the case of only TXR-18 (3 μM) and ODN-15 (6 μM), lane 2 represents the case of the compound (7a) (50 μM) and ImImPy (100 μM) added to TXR-18 (3 μM) and ODN-15 (6 μM), lane 3 represents the case of the compound (7a) (50 μM) and ImImIm (100 μM) added to TXR-18 (3 μM) and ODN-15 (6 μM), lane 4 represents the case of the compound (7a) (50 μM) and ImPyPy (100 μM) added to TXR-18 (3 μM) and ODN-15 (6 μM), and lane 5 represents the case of the compound (7a) (50 μM) and PyImPy (100 μM) added to TXR-18 (3 μM) and ODN-15 (6 μM).

Consequently, it was well observed that the crosslinked product was generated at a more or less low efficiency, in the system using ImImIm (Lane 3). However, almost no generation of any crosslinked product was observed in the systems, using the other triamides (Lanes 4 and 5). These results indicate a possibility that the interstrand-crosslinking reaction of DNA at an arbitrary sequence can progress on the basis of the model shown in FIG. 3.

Further, the optimum condition for the interstrand-crosslinking reaction was examined.

So as to make an experiment to examine the optimum interval between nucleotide sequences for the interstrand-crosslinking reaction with the compound (7a) and ImImPy, an experiment using the following base pair was done.

5'-[TXRed]-TTACAGTGGC-(T)$_n$-GCCAGCA-3'(SEQ ID NO: 8)

3'-GTCACCG-(A)$_n$-CGGTCGT-5'(SEQ ID NO: 11)

TXRed on the 5' terminus is Texas Red label.

When n is 0, the nucleotide sequence above is referred to as TXR-17, while the nucleotide sequence below is referred to as ODN-14. When n is 1, the nucleotide sequence above is referred to as TXR-18 while the nucleotide sequence below is referred to as ODN-15. When n is 2, the nucleotide sequence above is referred to as TXR-19, while the nucleotide sequence below is referred to as ODN-16. When n is 3, the nucleotide sequence above is referred to as TXR-20, while the nucleotide sequence below is referred to as ODN-17.

Figure 5:
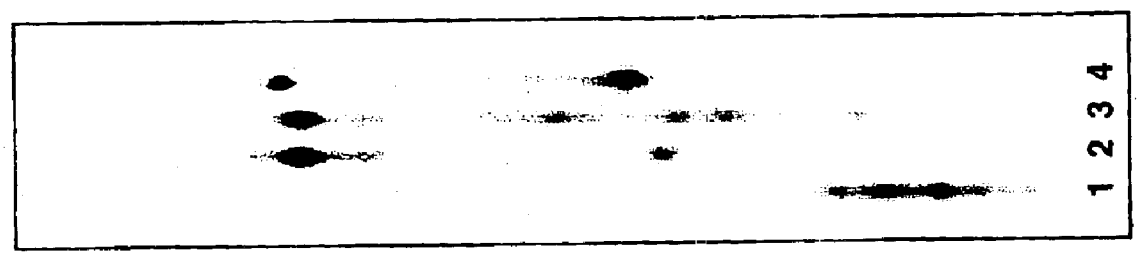
FIG. 5 is a photograph as a drawing substitute and shows the experimental results of the analysis of the interstrand-crosslinking reaction of the inventive compound, using DNAs of various lengths.

The results are shown in a photograph as a drawing substitute in FIG. 5. In FIG. 5, lane 1 represents the case of the compound (7a) (50 μM) and ImImPy (100 μM) added to TXR-17 (3 μM) and ODN-14(6 μM), at n=0, lane 2 represents the case of the compound (7a) (50 μM) and ImImPy (100 μM) added to TXR-18 (3 μM) and ODN-15(6 μM), at n=1, lane 3 represents the case of the compound (7a) (50 μM) and ImImPy (100 μM) added to TXR-19 (3 μM) and ODN-16(6 μM), at n=2, and lane 4 represents the case of the compound (7a) (50 μM) and ImImPy (100 μM) added to TXR-20 (3 μM) and ODN-17(6 μM), at n=3.

Consequently, no crosslinked product was confirmed at n=0 (lane 1). It was shown that quantitative interstrand-crosslinking reaction occurred, at n=2 (lane 3), as in the case at n=1 as previously described (lane 2). At n=3 (lane 4), however, the observed crosslinked product was at only about 20%.

Further, reaction conditions of reagent concentration and equivalent ratio were examined. Consequently, it could finally be confirmed that quantitative crosslinking reaction of Texas Red-18 (3 μM) occurred under conditions that the compound (7a) and ImImPy were individually lowered to 25 μM.

Consequently, cooperative interstrand-crosslinking reaction by the compound (7a) and ImImPy could be established.

Additionally, the design of the optimal triamide and crosslinker enables the creation of a tailor-made drug with a potency capable of selectively interstrand-crosslinking only the DNA site of an arbitrary nucleotide sequence.

A compound represented by the general formula in accordance with the invention:

(I)

(wherein, B represents a chemical structure capable of recognizing the nucleotide sequence of DNA; A represents a chemical structure capable of binding to one of the bases of DNA; L represents a linker by which the chemical structures of A and B can be linked to each other; X represents a spacer by which the A-L-B components can be linked to each other.), which can perform the interstrand-crosslinking of the double strands of DNA, has a structure such that two (A-L-B) components are linked together with spacer X.

The B moiety in the component (A-L-B) has a chemical structure capable of recognizing DNA nucleotide sequence, preferably a chemical structure derived from pyrrole optionally having a substituent (abbreviated as Py in the present specification) and/or imidazole optionally having a substituent (abbreviated as Im in the specification), which is preferably a chemical structure prepared by binding the pyrrole ring optionally having a substituent and the imidazole ring optionally having a substituent together, through an amide bond. Concerning the chemical structure of the moiety and the DNA nucleotide sequence binding thereto, known techniques can be referenced, including a) P. B. Dervan, et al., Nature, 282, 111–115 (1998); b) T. Fujiwara, Z.-F. Tao, Y. Ozeki, I. Saito, A. H.-J. Wang, M. Lee, H. Sugiyama, J. Am. Chem. Soc., 121, 7706–7707(1999).

The moiety A in the component (A-L-B) corresponds to the moiety with a chemical structure capable of binding to one of the bases of DNA, and the moiety A preferably can form a covalent bond with the bases in DNA. Preferably, the moiety A is an alkylated moiety of a DNA-alkylating anti-cancer antibiotic. More preferably, the moiety A has a chemical structure with cyclopropane ring or aziridine ring.

The linker L in the component (A-L-B) may satisfactorily be any of linkers capable of binding between the chemical structures of the moieties A and B, which works to integrate together the moiety for alkylating DNA base and the moiety capable of recognizing DNA nucleotide sequence. In other words, the linker can serve for specifically recognizing the moiety of a specific nucleotide sequence of DNA and specifically alkylating the base corresponding to the recognition site.

As the linker L, any linker of an appropriate length, namely of about 2 to 10, preferably about 2 to 5 atoms in length, is satisfactory, which is capable of chemically linking together the moieties A and B. Preferable linker L includes a chemical structure containing vinyl group.

Preferable (A-L-B) component includes those represented by the following formula (II):

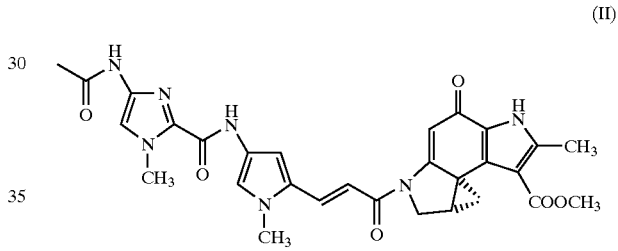
(II)

or the following formula (III):

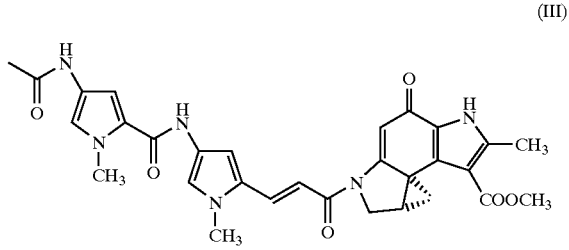
(III)

The spacer X binding the (A-L-B) component includes any spacers of an appropriate length, namely of about 1 to 15, preferably about 2 to 8 atoms in length, is preferable, which is capable of chemically binding together two of the (A-L-B) component. For example, the spacer X includes carbonyl group or acyl group derived from an organic dicarboxylic acid with 2 to 15 carbon atoms, preferably 2 to 8 carbon atoms. The organic dicarboxylic acid includes saturated or unsaturated aliphatic dicarboxylic acid, saturated or unsaturated alicyclic dicarboxylic acid, aromatic dicarboxylic acid, aromatic aliphatic dicarboxylic acid, and heterocyclic dicarboxylic acid.

The spacer X includes —CO— group, —CO—CH=CH—CO— group, —CO—(CH$_2$)$_4$—CO— group, or —CO—(p-C$_6$H$_4$)—CO— group. The spacer X is preferably acyl group of saturated aliphatic dicarboxylic acid, specifically including —CO—(CH$_2$)$_4$—CO— group.

The invention provides a method for interstrand-crosslinking a specific nucleotide sequence region of double-stranded DNA, using any of the inventive compounds described above. Preferably, the method of the invention is further carried out in the presence of a substance with a chemical structure capable of recognizing DNA nucleotide sequence, which includes triamides, for example ImImPy and ImImIm.

For interstrand-crosslinking by the method of the invention, the chemical structure of the moiety B which can recognize DNA nucleotide sequence in the component (A-L-B) can serve for the specific interstrand-crosslinking of a specific DNA nucleotide sequence region. For example, TGGC or GCCA in DNA or the complementary chains thereto can be interstrand-crosslinked by the compound (7a) when used as the inventive compound.

Still additionally, the invention provides an interstrand-crosslinking agent comprising the inventive compound for double-stranded DNA. The interstrand-crosslinking agent of the invention can highly efficiently progress the interstrand-crosslinking of a specific nucleotide sequence region of DNA.

Because the interstrand-crosslinking agent of the invention can progress interstrand-crosslinking of a specific nucleotide sequence region of DNA, the interstrand-crosslinking agent of the invention is useful for the therapeutic treatment or prophylaxis of various diseases due to gene abnormalities. The interstrand-crosslinking agent is particularly useful for the prophylaxis or therapeutic treatment of the expression of cancer gene. Thus, the invention provides a pharmaceutical composition comprising the inventive compound and a pharmaceutically acceptable carrier. The pharmaceutical composition of the invention is useful for the therapeutic treatment or prophylaxis of various diseases, for example, cancer caused by gene abnormalities.

The invention will be described below in examples, but the invention is not limited to these examples.

EXAMPLES

Example 1

Production of Compound (7a)

(I) Production of Compound (2)

A solution (5 ml) of 1-methyl-2-pyrrolealdehyde (3.0 g, 27.5 mmol) in acetic anhydride was gradually added dropwise to con. sulfuric acid (1.5 ml, 35.7 mmol) in acetic anhydride solution (3 ml), at −40° C. over 40 minutes. After the reaction mixture was agitated at −10° C. for 2 hours, hexane (100 ml) was added to the mixture. The resulting precipitate was collected, using a Kiriyama funnel, and was rinsed with hexane (10 ml×2), to recover a crude crystal in yellow (1.43 g, 34%). Without further purification, the crystal was immediately used for the next reaction.

Ethyl 2-diethylphosphonoacetate (1.93 ml, 9.75 mmol) was gradually added to a solution of sodium hydride (372 mg, 9.29 mmol, 60% oil suspension) in THF (5 ml), at 0° C. After further addition of a solution of 1-methyl-4-nitro-2-pyrrolealdehyde (1.43 g, 9.29 mmol) in THF (10 ml) at 0° C., the reaction mixture was agitated at ambient temperature for 2 hours. The solvents were distilled off from the reaction solution, to which was then added distilled water(10 ml). The aqueous layer was extracted, using ethyl acetate(100 ml×2). The organic layer was collected, dried over anhydrous sodium sulfate, filtered and concentrated, and the resulting residue was purified by silica gel column chromatography (25–50% EtOAc in hexane, gradient elution) to recover the compound (2) (1.69 g, 81%).

$^1$H NMR(CDCl$_3$) δ 1.34(t, J=7.0 Hz, 3H), 3.77(s, 3H), 4.26(q, J=7.0 Hz, 2H), 6.31(d, J=16.0 Hz, 1H), 7.11(d, J=1.5 Hz, 1H), 7.48(d, J=16.0 Hz, 1H), 7.56(d, J=1.5 Hz, 1H).

$^{13}$C NMR(CDCl$_3$) δ 14.3, 35.4, 60.8, 106.1, 118.4, 125.3, 129.8, 130.1, 136.7, 166.5.

MS(FAB+) 225[M$^+$].

(II) Production of Compound (3)

10% Palladium-carbon (220 mg) was added to a solution of the compound (2) (500 mg, 2.23 mmol) in anhydrous methanol (25 ml). Additionally, a solution of sodium borohydride (153 mg, 4.04 mmol) in distilled water (3 ml) was dropwise added at 0° C., and the resulting mixture was agitated at ambient temperature for 20 minutes. The reaction solution was filtered through Celite, followed by addition of ethyl acetate (500 ml). After the organic layer was rinsed in distilled water (10 ml), dried in anhydrous sodium sulfate, filtered and concentrated, a crude crystal in dark brown (461 mg) was recovered. Without further purification, the crystal was immediately used for the next reaction.

After ethyldiisopropylamine (0.52 ml, 2.98 mmol) and 1-methyl-4-nitro-2-trichloroacetylimidazole (O$_2$NImCOCCl$_3$) (550 mg, 2.02 mmol) separately prepared synthetically were sequentially added to a solution of the crude crystal in anhydrous methylene chloride (10 ml) at 0° C., the reaction mixture was agitated at ambient temperature for one hour. The solvents were distilled off from the reaction solution, and the resulting residue was purified by silica gel column chromatography (30–50% EtOAc (in hexane)) to recover the compound (3) (400 mg, 52% for 2 steps).

$^1$H NMR(CDCl$_3$) δ 1.33 (t, J=7.0 Hz, 3H), 3.71(s, 3H), 4.21(s, 3H), 4.25(q, J=7.0 Hz, 2H), 6.16 (d, J=16.0 Hz, 1H), 6.62(d, J=1.5 Hz, 1H), 7.32(d, J=1.5 Hz, 1H), 7.55(d, J=16.0 Hz, 1H), 7.82(s, 1H), 8.97(brs, 1H).

$^{13}$C NMR(CDCl$_3$) δ 14.3, 34.4, 37.1, 60.3, 102.5, 114.2, 117.9, 122.1, 124.4, 127.6, 131.4, 137.2, 145.3, 154.4, 167.4.

MS(FAB+) 347[M+].

(III) Production of Compound (4a)

10% Palladium-carbon (120 mg) was added to a solution of the compound (3) (250 mg, 0.72 mmol) in anhydrous methanol-ethyl acetate (1:1, 10 ml). Additionally, a solution of sodium borohydride (54.5 mg, 1.44 mmol) in distilled water (0.5 ml) was dropwise added at 0° C., and the resulting mixture was agitated at ambient temperature for 20 minutes. The reaction solution was filtered by silica gel column chromatography (EtOAc), and the solvents were distilled off to recover a crude crystal in dark brown (141 mg). Without further purification, the crystal was immediately used for the next reaction.

Ethyldiisopropylamine (0.25 ml, 1.33 mmol) and adipoyl dichloride (32 µl, 0.22 mmol) were sequentially added to a solution of the crude crystal in anhydrous methylene chloride (2 ml) at 0° C., and the resulting mixture was agitated at ambient temperature for 14 hours. The solvents were distilled off from the reaction solution, and the resulting residue in yellow was purified by silica gel column chromatography (0–3% MeOH in CHCl$_3$) to recover the compound (4a) (96.2 mg, 36% for 2 steps).

$^1$H NMR(CDCl$_3$) δ 1.32(t, J=6.5 Hz, 6H), 1.81(s, 4H), 2.42(s, 4H), 3.67(s, 6H), 4.04(s, 6H), 4.24(q, J=6.5 Hz, 4H), 6.10(d, J=15.5 Hz, 2H), 6.51(s, 2H), 7.34(s, 2H), 7.41(s, 2H), 7.53(d, J=15.5 Hz, 2H), 8.04(brs, 2H), 8.80(brs, 2H).

$^{13}$C NMR(5% CD$_3$OD in CDCl$_3$) δ 14.1, 24.8, 34.1, 34.5, 34.6, 60.3, 102.3, 112.9, 114.3, 118.0, 122.8, 127.1, 131.8, 133.7, 135.8, 155.8, 168.0, 171.0.

MS(ESI+) 744.6[M$^+$].

(VI) Production of Compound (5a)

1,8-Diazabicyclo[5.4.0]undec-7-ene (DBU) (0.6 ml, 4.01 mmol) was added to a suspension of 4a (76.2 mg, 0.10 mmol) in distilled water (0.6 ml), and the resulting reaction solution was agitated at ambient temperature for 15 hours.

The termination of the reaction was confirmed by HPLC (0–100% 50 mmol aqueous ammonium formate solution-acetonitrile, 20 min, 254 nm), and thereafter, the solvents were distilled off from the reaction solution to recover a dark brown residue, which was then crystallized, using diethyl ether (10 ml) and ethyl acetate (10 ml). The resulting DBU salt compound was desalted, using dilute 1% hydrochloric acid, and the resulting precipitate was collected through a Kiriyama funnel, which was then dried under reduced pressure, to recover 5a (40.0 mg, 57%).

$^1$H NMR(DMSO-d$_6$) δ 1.58(s, 4H), 2.32(s, 4H), 3.68(s, 6H), 3.94(s, 6H), 6.03(d, J=15.5 Hz, 2H), 6.80(s, 2H), 7.41(s, 2H), 7.43(s, 2H), 7.46(d, J=15.5 Hz, 2H), 9.89(brs, 2H), 10.24 (brs, 2H).

MS(ESI+) 688.5[M+].

(V) Production of Compound (6a)

1,1'-Carbonyldiimidazole (CDI) (42 mg, 261 μmol) was added to a solution of 5a (30.0 mg, 43.6 μmol) in anhydrous dimethylformamide (1 ml), and the resulting reaction solution was agitated at ambient temperature for 15 hours. The solvents were distilled off from the reaction solution, to recover a residue in yellow, which was then crystallized using diethyl ether (10 ml), to recover the compound (6a) (35.7 mg, 100%).

$^1$H NMR(DMSO-d$_6$) δ 1.59(s, 4H), 2.34(s, 4H), 3.78(s, 6H), 3.96(s, 6H), 7.11(s, 2H), 7.16(d, J=14.5 Hz, 2H), 7.32(s, 2H), 7.45(s, 2H), 7.49(s, 2H), 7.87(d, J=14.5 Hz, 2H), 7.90(s, 2H), 8.68(s, 2H), 10.07(brs, 2H), 10.23(brs, 2H).

(IV) Production of Compound (7a)

To a solution of sodium hydride (2.6 mg, 64.4 μmol, 60% oil suspension) in anhydrous dimethylformamide (0.2 ml) was added a solution of the segment A (12.5 mg, 48.3 μmol) of separately prepared DU86 in anhydrous dimethylformamide (0.2 ml) at 0° C. Subsequently, a solution of the compound (6a) (13.6 mg, 17.2 μmol) in anhydrous dimethylformamide (0.2 ml) was added to the resulting mixture. Then, the resulting reaction solution was agitated at 0° C. for 4 hours. To the reaction solution was added 10 mM sodium phosphate (2 ml) buffer solution at 0° C., from which the solvents were distilled off under reduced pressure, to recover a residue in yellow. The crude crystal was rinsed sequentially with distilled water (10 ml), methanol (10 ml), and diethyl ether (10 ml) on a Kiriyama funnel, and dried under reduced pressure, to recover the entitled compound (7a) (12.2 mg, 61%).

$^1$H NMR(DMSO-d$_6$) δ 1.29(m, 2H), 1.58(s, 4H), 2.09(m, 2H), 2.33(s, 4H), 2.47(s, 6H), 3.45(m, 2H), 3.72(s, 6H), 3.73(s, 6H), 3.95(s, 6H), 4.18(m, 2H), 4.28(m, 2H), 6.57(d, J=14.5 Hz, 2H), 6.83(brs, 2H), 6.99(s, 2H), 7.41(s, 2H), 7.44(s, 2H), 7.58(d, J=14.5 Hz, 2H), 9.98(s, 2H), 10.23(s, 2H), 12.36(brs, 2H).

MS(ESI+) 1168.6[M$^+$].

Example 2

Production of Compound (7b)

(I) Production of Compound (4b)

10% Palladium-carbon (200 mg) was added to a solution of the compound (3) (420 mg, 1.21 mmol) produced in Example 1-(2) in a mixture of anhydrous methanol-ethyl acetate (1:1, 30 ml). After further dropwise addition of a solution of sodium borohydride (106 mg, 2.80 mmol) in distilled water (1 ml) at 0° C., the reaction mixture was agitated at ambient temperature for 20 minutes. After the reaction solution was filtered by silica gel column chromatography (EtOAc), the solvents were distilled off to recover a crude crystal in dark brown (327 mg). Without further purification, the crystal was immediately used for the next reaction.

Ethyldiisopropylamine (0.6 ml, 3.63 mmol) and terephthaloyl dichloride (122 mg, 0.61 mmol) were sequentially added to a solution of the crude crystal in anhydrous methylene chloride (10 ml) at 0° C., and the resulting mixture was agitated at ambient temperature for 2 hours. The solvents were distilled off from the reaction solution, and the resulting residue in yellow was purified by silica gel column chromatography (0–3% MeOH in CHCl$_3$) to recover the compound (4b) (223 mg, 48% for 2 steps).

$^1$H NMR(CDCl$_3$) δ 1.33(t, J=7.5 Hz, 6H), 3.71(s, 6H), 4.12(s, 6H), 4.25(q, J=7.5 Hz, 4H), 6.13(d, J=16.0 Hz, 2H), 6.55(s, 2H), 7.38(s, 2H), 7.56(d, J=16.0 Hz, 2H), 7.61(s, 2H), 8.02(s, 4H), 8.38(brs, 2H), 8.82(brs, 2H).

(II) Production of Compound (5b)

1,8-Diazabicyclo[5.4.0]undec-7-ene (DBU) (0.2 ml, 1.34 mmol) was added to a suspension of the compound (4b) (30.0 mg, 0.04 mmol) in distilled water (0.2 ml), and the resulting reaction solution was agitated at ambient temperature for 12 hours. The termination of the reaction was confirmed by HPLC (0–100% 50 mmol, aqueous ammonium formate solution-acetonitrile, 20 min, 254 nm), and thereafter, the solvents were removed from the reaction solution to recover a dark brown residue, which was then crystallized, using diethyl ether (10 ml) and ethyl acetate (10 ml). The resulting DBU salt compound was desalted, using dilute 1% hydrochloric acid, and the resulting precipitate was collected through a Kiriyama funnel, which was then dried under reduced pressure, to recover the compound (5b) (21.5 mg, 85%).

$^1$H NMR(DMSO-d$_6$) δ 3.68(s, 6H), 4.00(s, 6H), 6.04(d, J=16.0 Hz, 2H), 6.81(s, 2H), 7.43(s, 2H), 7.46(d, J=16.0 Hz, 2H), 7.66(s, 2H), 8.10(s, 4H), 9.95(s, 2H), 10.95(s, 2H).

(III) Production of Compound (6b)

CDI (76mg, 231 μmol) was added to a solution of the compound (5b) (54.5 mg, 79.9 μmol) in anhydrous dimethylformamide (3 ml), and the resulting reaction solution was agitated at ambient temperature for 15 hours. The solvents were distilled off from the reaction solution, to recover a residue in yellow, which was then crystallized using diethyl ether (10 ml), to recover the compound (6b) (63.0 mg, 97%).

$^1$H NMR(DMSO-d$_6$) δ 3.79(s, 6H), 4.02(s, 6H), 7.10(s, 2H), 7.17(d, J=15.0 Hz, 2H), 7.32(s, 2H), 7.50(s, 2H), 7.68(s, 2H), 7.87(d, J=15.0 Hz, 2H), 7.90(s, 2H), 8.11(s, 4H), 8.67(s, 2H), 10.15(s, 2H), 10.96 (s, 2H).

(VI) Production of Compound (7b)

To a solution of sodium hydride (4.5 mg, 112.5 μmol, 60% oil suspension) in anhydrous dimethylformamide (0.1 ml) was added a solution of the segment A (21.0 mg, 81.3 μmol) of separately prepared DU86 in anhydrous dimethylformamide (0.1 ml) at 0° C. Subsequently, a solution of the compound (6b) (21.0 mg, 24.9 μmol) in anhydrous dimethylformamide (0.8 ml) was added to the resulting mixture. Then, the resulting reaction solution was agitated at 0° C. for 18 hours. To the reaction solution was added 10 mM sodium phosphate (2 ml) buffer solution at 0° C., from which the solvents were distilled off under reduced pressure, to recover a residue in yellow. The crude crystal was rinsed sequentially with distilled water (10 ml), methanol (10 ml), and diethyl ether (10 ml) on a Kiriyama funnel, and dried under reduced pressure, to recover the entitled compound (7b) (24.5 mg, 83%).

$^1$H NMR(DMSO-d$_6$) δ 1.30(m, 2H), 2.09(m, 2H), 2.47(s, 6H), 3.46(m, 2H), 3.74(s, 12H), 4.02(s, 6H), 4.20(m, 2H), 4.29(m, 2H), 6.60(d, J=15.0 Hz, 2H), 6.83(brs, 2H), 7.01(s, 2H), 7.43(s, 2H), 7.58(d, J=15.0 Hz, 2H), 7.68(s, 2H), 8.12(s, 4H), 10.05(s, 2H), 10.96(s, 2H), 12.36(brs, 2H).

MS(ESI+) 1188.9[M+].

Example 3

Production of Compound (7c)

(I) Production of Compound (4c)

10% Palladium-carbon (100 mg) was added to a solution of the compound (3) (200 mg, 0.58 mmol) produced in Example 1-(2) in a mixture of anhydrous methanol-ethyl acetate (1:1, 20 ml). After further dropwise addition of a solution of sodium borohydride (44 mg, 1.15 mmol) in distilled water (0.5 ml) at 0° C., the reaction mixture was agitated at ambient temperature for 20 minutes. After the reaction solution was filtered by silica gel column chromatography (EtOAc), the solvents were distilled off to recover a crude crystal in dark brown (93 mg). Without further purification, the crystal was immediately used for the next reaction.

Ethyldiisopropylamine (0.15 ml, 0.88 mmol) and fumaryl dichloride (fumaryl chloride) (16 μl, 0.15 mmol) were sequentially added to a solution of the crude crystal in anhydrous methylene chloride (2 ml) at 0° C., and the resulting mixture was agitated at ambient temperature for 12 hours. The solvents were distilled off from the reaction solution, and the resulting residue in yellow was purified by silica gel column chromatography (0–3% MeOH in $CHCl_3$) to recover the compound (4c) (50.1 mg, 41% for 2 steps).

$^1$H NMR(DMSO-$d_6$) δ 1.25(t, J=7.0 Hz, 6H), 3.70(s, 6H), 3.98(s, 6H), 4.16(q, J=7.0 Hz, 4H), 6.11(d, J=16.0 Hz, 2H), 6.85(s, 2H), 7.26(s, 2H), 7.45(s, 2H), 7.52(d, J=16.0 Hz, 2H), 7.61(s, 2H), 9.97(s, 2H), 10.90(s, 2H).

(II) Production of Compound (5c)

A reaction solution of DBU (0.3 ml, 2.00 mmol) added to a suspension of the compound 4c (40.1 mg, 0.06 mmol) in distilled water (0.3 ml) was agitated at ambient temperature for 17 hours. The termination of the reaction was confirmed by HPLC (0–100% aqueous 50 mmol ammonium formate solution—acetonitrile, 20 min, 254 nm), and thereafter, the solvents were distilled off from the reaction solution to recover a dark brown residue, which was then crystallized, using diethyl ether (10 ml) and ethyl acetate (10 ml). The resulting DBU salt compound was desalted, using dilute 1% hydrochloric acid, and the resulting precipitate was collected through a Kiriyama funnel, which was then dried under reduced pressure, to recover the compound (5c) (22.5 mg, 61%).

$^1$H NMR(DMSO-$d_6$) δ 3.69(s, 6H), 3.98(s, 6H), 6.04(d, J=16.0 Hz, 2H), 6.83(s, 2H), 7.26(s, 2H), 7.43(s, 2H), 7.47(d, J=16.0 Hz, 2H), 7.60(s, 2H), 9.97(s, 2H), 10.90(s, 2H).

(III) Production of Compound (6c)

CDI (30 mg, 185 μmol) was added to a solution of the compound (5c) (17.5 mg, 26.5 μmol) in anhydrous dimethylformamide (1 ml), and the resulting reaction solution was agitated at ambient temperature for 15 hours. The solvents were distilled off from the reaction solution, to recover a residue in yellow, which was then crystallized using diethyl ether (10 ml), to recover the compound (6c) (18.5 mg, 92%).

$^1$H NMR(DMSO-$d_6$) δ 3.78(s, 6H), 4.00(s, 6H), 7.11(s, 2H), 7.17(d, J=15.0 Hz, 2H), 7.28(s, 2H), 7.34(s, 2H), 7.52(s, 2H), 7.63(s, 2H), 7.89(d, J=15.0 Hz, 2H), 7.91(s, 2H), 8.68(s, 2H), 10.17(s, 2H), 10.89(s, 2H).

(VI) Production of Compound (7c)

To a solution of sodium hydride (2.8 mg, 71.2 μmol, 60% oil suspension) in anhydrous dimethylformamide (0.1 ml) was added a solution of the segment A (13.8 mg, 53.4 μmol) of separately prepared DU86 in anhydrous dimethylformamide (0.1 ml) at 0° C. Subsequently, a solution of the compound (6c) (13.5 mg, 17.8 μmol) in anhydrous dimethylformamide (0.7 ml) was added to the resulting mixture. Then, the resulting reaction solution was agitated at 0° C for 12 hours. To the reaction solution was added 10 mM sodium phosphate (2 ml) buffer solution at 0° C., from which the solvents were distilled off under reduced pressure, to recover a residue in yellow. The crude crystal was rinsed sequentially with distilled water (10 ml), methanol (10 ml), and diethyl ether (10 ml) on a Kiriyama funnel, and dried under reduced pressure, to recover the entitled compound (7c) (9.6 mg, 47%).

$^1$H NMR(DMSO-$d_6$) δ 1.30(m, 2H), 2.08(m, 2H), 2.47(s, 6H), 3.47(m, 2H), 3.73(s, 6H), 3.74(s, 6H), 3.99(s, 6H), 4.20(m, 2H), 4.29(m, 2H), 6.59(d, J=15.0 Hz, 2H), 6.79(brs, 2H), 7.01(s, 2H), 7.28(s, 2H), 7.43(s, 2H), 7.58(d, J=15.0 Hz, 2H), 7.61(s, 2H), 10.07(s, 2H), 10.89(s, 2H), 12.36(brs, 2H).

MS(ESI+) 1138.5[M$^+$].

Example 4

Production of Compound (7d)

(I) Production of Compound (4d)

10% Palladium-carbon (100 mg) was added to a solution of the compound (3) (200 mg, 0.58 mmol) produced in Example 1-(2) in a mixture of anhydrous methanol-ethyl acetate (1:1, 20 ml). After further dropwise addition of a solution of sodium borohydride (44 mg, 1.15 mmol) in distilled water (0.5 ml) at 0° C., the reaction mixture was agitated at ambient temperature for 20 minutes. After the reaction solution was filtered by silica gel column chromatography (EtOAc), the solvents were distilled off to recover a crude crystal in dark brown (63 mg). Without further purification, the crystal was immediately used for the next reaction.

CDI (16 mg, 0.10 mmol) was added to a solution of the crude crystal in anhydrous methylene chloride (2 ml) at 0° C., and the resulting mixture was agitated at ambient temperature for 12 hours. The solvents were distilled off from the reaction solution, and the resulting residue in yellow was purified by silica gel column chromatography (0–3% MeOH in $CHCl_3$), to recover the compound (4d) (51.3 mg, 45% for 2 steps).

$^1$H NMR(DMSO-$d_6$) δ 1.24(t, J=7.0 Hz, 6H), 3.70(s, 6H), 3.96(s, 6H), 4.15(q, J=7.0 Hz, 4H), 6.08(d, J=16.0 Hz, 2H), 6.87(s, 2H), 7.26(s, 2H), 7.45(s, 2H), 7.51(d, J=16.0 Hz, 2H), 8.31(brs, 2H), 10.10(s, 2H).

(II) Production of Compound (5d)

DBU (0.3 ml, 2.00 mmol) was added to a suspension of 4d (41.3 mg, 0.06 mmol) in distilled water (0.3 ml), and the resulting reaction solution was agitated at ambient temperature for 17 hours. The termination of the reaction was confirmed by HPLC (0–100% aqueous 50 mmol ammonium formate solution—acetonitrile, 20 min, 254 nm), and thereafter, the solvents were distilled off from the reaction solution to recover a dark brown residue, which was then crystallized, using diethyl ether (10 ml) and ethyl acetate (10 ml). The resulting DBU salt compound was desalted, using dilute 1% hydrochloric acid, and the resulting precipitate was collected through a Kiriyama funnel, which was then dried under reduced pressure, to recover the compound (5d) (27.4 mg, 73%).

$^1$H NMR(DMSO-$d_6$) δ 3.68(s, 6H), 3.96(s, 6H), 6.01(d, J=16.0 Hz, 2H), 6.84(s, 2H), 7.26(s, 2H), 7.42(s, 2H), 7.47(d, J=16.0 Hz, 2H), 8.84(brs, 2H), 10.08(s, 2H).

(III) Production of Compound (6d)

CDI (30 mg, 185 μmol) was added to a solution of compound (5d) (22.4mg, 37.1 μmol) in anhydrous dimethylformamide (1 ml), and the resulting reaction solution was agitated at ambient temperature for 15 hours. The solvents were distilled off from the reaction solution, to recover a residue in yellow, which was then crystallized using diethyl ether (10 ml), to recover the compound (6d) (25.2 mg, 96%).

¹H NMR(DMSO-d₆) δ 3.79(s, 6H), 3.98(s, 6H), 7.10(s, 2H), 7.15(d, J=15.0 Hz, 2H), 7.28(s, 2H), 7.34(s, 2H), 7.50(s, 2H), 7.87(d, J=15.0 Hz, 2H), 7.90(s, 2H), 8.67(s, 2H), 8.89(brs, 2H), 10.25(s, 2H).

(VI) Production of Compound (7d)

To a solution of sodium hydride (4.6 mg, 114.4 μmol, 60% oil suspension) in anhydrous dimethylformamide (0.1 ml) was added a solution of the segment A (22.1 mg, 85.8 μmol) of separately prepared DU86 in anhydrous dimethylformamide (0.1 ml) at 0° C. Subsequently, a solution of the compound (6d) (20.2 mg, 28.6 μmol) in anhydrous dimethylformamide (0.1 ml) was added to the resulting mixture. Then, the resulting reaction solution was agitated at 0° C. for 12 hours. To the reaction solution was added 10 mM sodium phosphate (2 ml) buffer solution at 0° C., from which the solvents were distilled off under reduced pressure, to recover a residue in yellow. The crude crystal was rinsed sequentially with distilled water (10 ml), methanol (10 ml), and diethyl ether (10 ml) on a Kiriyama funnel, and dried under reduced pressure, to recover the entitled compound (7d) (5.5 mg, 18%).

¹H NMR(DMSO-d₆) δ 1.29(m, 2H), 2.09(m, 2H), 2.47(s, 6H), 3.44(m, 2H), 3.72(s, 6H), 3.73(s, 6H), 3.97(s, 6H), 4.18(m, 2H), 4.27(m, 2H), 6.56(d, J=14.5 Hz, 2H), 6.84(brs, 2H), 7.01(s, 2H), 7.26(s, 2H), 7.42(s, 2H), 7.57(d, J=14.5 Hz, 2H), 8.82(brs, 2H), 10.16(s, 2H), 12.35(brs, 2H).

MS(ESI+) 1084.5[M⁺].

Example 5

Production of ImImPy (Compound (II))

(I) Production of O₂NPyLCONHCH₂CH₂CH₂NMe₂ (compound (8))

After dimethylaminopropylamine (1 ml, 8.33 mmol) was added to O₂NPyLCOCCl₃ (500 mg, 1.84 mmol), the reaction mixture was agitated at ambient temperature for 12 hours. After the solvents were distilled off from the reaction solution, the recovered yellow residue was crystallized, using diethyl ether (3 ml), to recover the compound (8) (460 mg, 97%).

¹H NMR(CDCl₃) δ 1.75(t, J=6.0 Hz, 2H), 2.34(s, 6H), 2.54(t, J=6.0 Hz, 2H), 3.49(q, J=6.0 Hz, 2H), 4.00(s, 3H), 6.94(s, 1H), 7.52(s, 1H), 8.68(brs, 1H).

(II) Production of O₂NImPyLCONHCH₂CH₂CH₂NMe₂ (Compound (9))

10% Palladium-carbon (120 mg) was added to a solution of the compound (8) (460 mg, 1.81 mmol) in anhydrous methanol (3 ml), and the resulting mixture was agitated at hydrogen pressure at ambient temperature for 2 hours. After the reaction solution was filtered through Celite (MeOH), the solvents were distilled off, to recover a crude crystal in yellow (413 mg). Without further purification, the crystal was immediately used for the next reaction.

To a solution of the crude crystal in anhydrous methylene chloride (8 ml) were sequentially added ethyldiisopropylamine (0.5 ml, 2.87 mmol) and separately prepared O₂NImCOCCl₃ (493 mg, 1.81 mmol) at 0° C., and the resulting mixture was agitated at ambient temperature for 15 hours. The solvents were distilled off from the reaction solution, and to the resulting residue was added distilled water (30 ml). The resulting precipitate in yellow was filtered and recovered, using a Kiriyama funnel. The precipitate was rinsed sequentially with distilled water (30 ml) and diethyl ether (5 ml), and dried under reduced pressure, to recover the compound (9) (587 mg, 86% for 2 steps).

¹H NMR(DMSO-d₆) δ 1.61(t, J=7.0 Hz, 2H), 2.14(s, 6H), 2.24(t, J=7.0 Hz, 2H), 3.19(q, J=7.0 Hz, 2H), 3.81(s, 3H), 4.04(s, 3H), 6.97(s, 1H), 7.27(s, 1H), 8.14(brs, 1H), 8.61(s, 1H), 10.80(brs, 1H).

(III) Production of O₂NImImPyLCONHCH₂CH₂CH₂NMe₂ (Compound (10))

10% Palladium-carbon (50 mg) was added to a solution of the compound (9) (100 mg, 0.27 mmol) in anhydrous methanol (3 ml), and the resulting mixture was agitated at hydrogen pressure and ambient temperature for 4 hours. After the reaction solution was filtered through Celite (MeOH), the solvents were distilled off, to recover a crude crystal in yellow (65.3 mg). Without further purification, the crystal was immediately used for the next reaction.

To a solution of the crude crystal in anhydrous methylene chloride (2 ml) were sequentially added ethyldiisopropylamine (0.1 ml, 0.57 mmol) and separately prepared O₂NImCOCCl₃ (72.2 mg, 0.27 mmol) at 0° C., and the resulting mixture was agitated at ambient temperature for 15 hours. The solvents were distilled off from the reaction solution, and to the resulting residue was added distilled water (10 ml). The resulting precipitate in yellow was filtered and recovered, using a Kiriyama funnel. The precipitate was rinsed sequentially with distilled water (10 ml) and diethyl ether (2 ml), and dried under reduced pressure, to recover the compound (10) (58.2 mg, 44% for 2 steps).

¹H NMR(DMSO-d₆) δ 1.61(t, J=7.0 Hz, 2H), 2.15(s, 6H), 2.25(t, J=7.0 Hz, 2H), 3.19(q, J=7.0 Hz, 2H), 3.80(s, 3H), 4.04(s, 3H), 4.06(s, 3H), 6.91(s, 1H), 7.23(s, 1H), 7.58(s, 1H), 8.13(brs, 1H), 8.65(s, 1H), 10.29(s, 1H).

(VI) Production of AcHNImImPyLCONHCH₂CH₂CH₂NMe₂ (Compound (11))

10% Palladium-carbon (40 mg) was added to a solution of the compound (10) (48.2 mg, 96.4 μmol) in anhydrous methanol-ethyl acetate (2:1, 6 ml). Additionally, a solution of sodium borohydride (8 mg, 0.21 mmol) in distilled water (0.4 ml) was dropwise added at 0° C., and the resulting mixture was agitated at ambient temperature for 20 minutes. The reaction solution was filtered through Celite (MeOH), from which the solvents were distilled off to recover a crude crystal in yellow (38 mg). Without further purification, the crystal was immediately used for the next reaction.

After ethyldiisopropylamine (0.1 ml, 0.57 mmol) and acetic anhydride (0.1 ml, 1.05 mmol) were added to the crude crystal, the resulting mixture was agitated at ambient temperature for 4 hours. The solvents were distilled off from the reaction solution, and to the resulting residue was added chloroform (1 ml), to generate insoluble matters, which were then removed by filtration. To the crude crystal recovered after solvent distillation was added diethyl ether (2ml), for rinsing. The crystal was dried under reduced pressure, to recover the entitled compound (11) (23.2 mg, 47% for 2 steps).

¹H NMR(DMSO-d₆) δ 1.61(m, 2H), 2.04(s, 3H), 2.14(s, 6H), 2.25(m, 2H), 3.19(m, 2H), 3.81(s, 3H), 3.98(s, 3H), 4.00(s, 3H), 6.92(s, 1H), 7.23(s, 1H), 7.51(s, 1H), 7.56(s, 1H), 8.12(brs, 1H), 9.34(s, 1H), 10.27(s, 1H), 10.30(s, 1H).

Example 6

Analysis Using Polyacrylamide Gel Electrophoresis

To 5 mM sodium cacodylate buffer, pH 7.0 in total volume of 10 μl was added a standard reaction solution containing 3 μM of DNA fragment with the 5'-terminus labeled with Texas Red, 6 μM of an oligomer complementary to the DNA, 20 v/v % DMF and a chemical substance at a concentration defined above, in a small-volume centrifuge (Eppendorf) tube, which was then left to stand overnight at 37° C. After 110 μl of distilled water purified with Milli-Q was added to the mixture for dilution, 1 μl of the dilution was drawn out. The solution (1 μl) was centrifuged under reduced pressure to recover DNA, which was dissolved in a loading dye (a DMF solution of Fusion Red) (8 µl). 2 µl of the solution was subjected to electrophoresis on 15% denatured polyacrylamide gel, using HITACHI 5500-S DNA sequencer system.

Example 7

Structure Confirmation Test of Interstrand Crosslinked Product

To 5 mM sodium cacodylate buffer, pH 7.0 in total volume of 10 µl was added a standard reaction solution containing 3 µM of DNA fragment with the 5'-terminus labeled with Texas Red, 6 µM of an oligomer complementary to the DNA, 20 v/v % DMF and a chemical substance at a concentration defined above, in a small-volume centrifuge (Eppendorf) tube, which was then left to stand overnight at 37° C.

1 µl of the reaction solution was taken out, to which was added Milli-Q of 11 µl for dilution. 1 µl of the dilution was drawn out for use on Lanes 2 and 7. The dilution solution (11 µl) was shaked at 90° C. for 20 minutes, followed by addition of piperidine (1 µl) for shaking at 90° C. for 20 minutes. After the solution was centrifuged under reduced pressure, the solution was further freeze-dried overnight. Then, 1 µl of 50 mM sodium cacodylate buffer, pH 7.0 and 10 µl of Milli-Q were added to the freeze-dried product for dilution. 1 µl of the dilution was taken out for Lanes 3 and 8. After Ap (1 µl) was added to the solution (10 µl) for shaking at 37° C. for 2 hours, 1.1 µl of the resulting solution was taken out for use on Lanes 4 and 9.

The individual reaction solutions taken out were centrifuged under reduced pressure to recover DNA, which were dissolved in 8 µl of a loading dye (Fusion Red in DMF solution). 2 µl of the resulting solution was subjected to electrophoresis on 15% denatured polyacrylamide gel using HITACH 5500-S DNA sequencer system.

Example 8

Nucleotide Sequence Specificity Test of Interstrand-crosslinked Product

To 5 mM sodium cacodylate buffer, pH 7.0 in total volume of 10 µl was added a standard reaction solution containing 3 µM of DNA fragment with the 5'-terminus labeled with Texas Red, 6 µM of each DNA oligomer, 20 v/v % DMF and a chemical substance at a concentration defined above, in a small-volume centrifuge (Eppendorf) tube, which was then left to stand overnight at 37° C. After 110 µl of distilled water purified with Milli-Q was added to the mixture for dilution, 1 µl of the dilution was drawn out. The solution (1 µl) was centrifuged under reduced pressure to recover DNA, which was dissolved in a loading dye (a DMF solution of Fusion Red) (8 µl). 2 µl of the solution was subjected to electrophoresis on 15% denatured polyacrylamide gel using HITACHI 5500-S DNA sequencer system.

Example 9

Test of Optimum Conditions for Interstrand-crosslinking Reaction

To 5 mM sodium cacodylate buffer, pH 7.0 in total volume of 10 µl was added a standard reaction solution containing 3 µM of each DNA fragment with the 5'-terminus labeled with Texas Red, 6 µM of a DNA oligomer complementary to the fragment, 20 v/v % DMF and a chemical substance at a concentration defined above, in a small-volume centrifuge (Eppendorf) tube, which was then left to stand overnight at 37° C. After 110 µl of distilled water purified with Milli-Q was added to the mixture for dilution, 1 µl of the dilution was drawn out. The solution (1 µl) was centrifuged under reduced pressure to recover DNA, which was dissolved in a loading dye (a DMF solution of Fusion Red) (8 µl). 2 µl of the solution was subjected to electrophoresis on 15% denatured polyacrylamide gel using HITACHI 5500-S DNA sequencer system.

Example 10

Test of Reaction Conditions for Reagent Concentration and Equivalent Ratio

To 5 mM sodium cacodylate buffer, pH 7.0 in total volume of 10 µl was added a standard reaction solution containing 3 µM of a DNA fragment (TXR-18) with the 5'-terminus labeled with Texas Red, 6 µM of a DNA oligomer (ODN-15) complementary to the fragment, 20 v/v % DMF and a chemical substance at a concentration defined above, in a small-volume centrifuge (Eppendorf) tube, which was then left to stand overnight at 37° C. [7a (µM), ImImPy (µM); 50, 100 (Lane 1); 25, 50 (Lane 2); 12, 25 (Lane 3); 6, 12 (Lane 4); 3, 6 (Lane 5); 25, 100 (Lane 6); 25, 50 (Lane 7); 25, 25 (Lane 8); 25, 12 (Lane 9); 25, 6 (Lane 10)]

After 110 µl of distilled water purified with Milli-Q was added to the mixture for dilution, 1 µl of the dilution was drawn out. The solution (1 µl) was centrifuged under reduced pressure, to recover DNA, which was dissolved in a loading dye (a DMF solution of Fusion Red) (8 µl). 2 µl of the solution was subjected to electrophoresis on 15% denatured polyacrylamide gel using HITACHI 5500-S DNA sequencer system.

Figure 6:
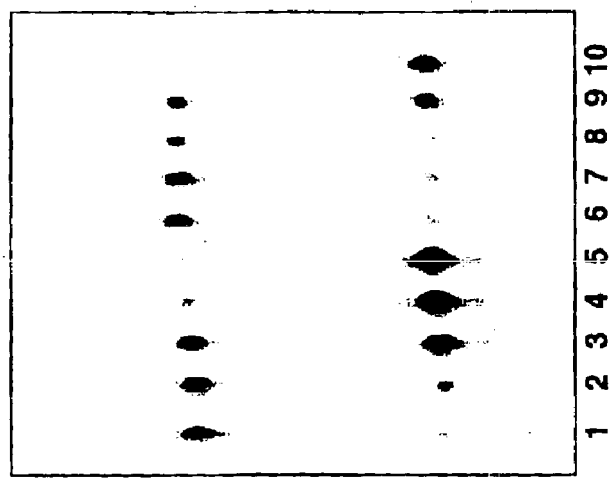
FIG. 6 is a photograph as a drawing substitute and shows the results of crosslinking reaction at various concentrations of the inventive compound (7a) and ImImPy.

The results are shown in FIG. 6. The concentrations of 7a (µM) and ImImPy (µM) on the individual lanes in FIG. 6 are as described above.

Figure 7:
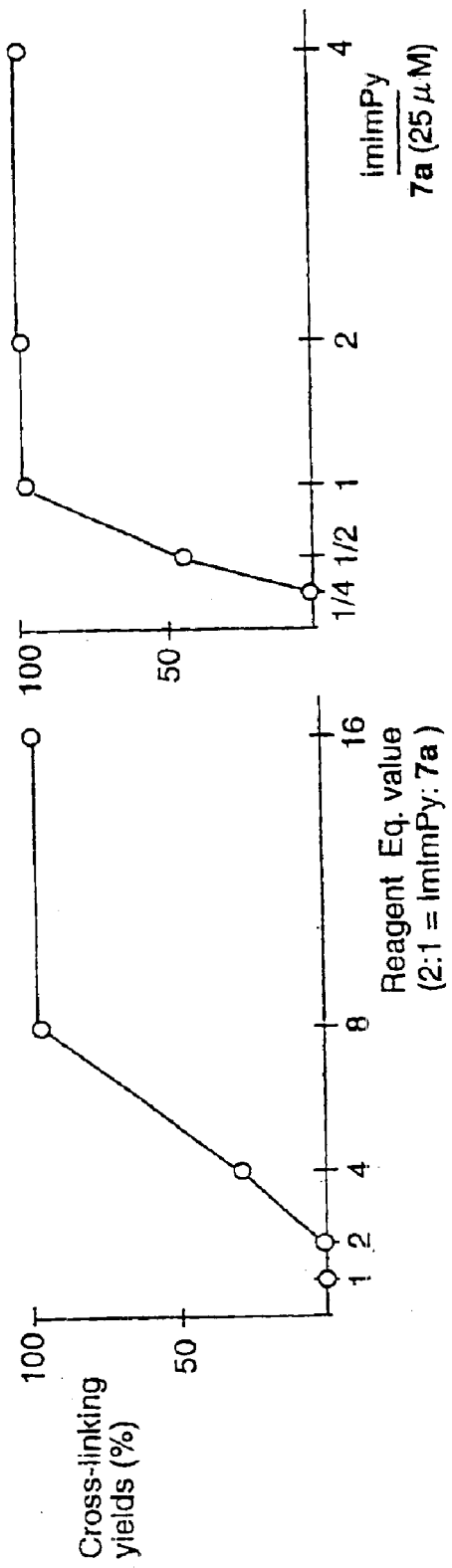
FIG. 7 shows graphs of crosslinking yields under various conditions, using the inventive compound (7a) and ImImPy.

Additionally, the crosslinking yield is shown in FIG. 7. The amount of sample in equivalent is shown on the left side of FIG. 7, in case of ImImPy : 7a=2:1, and the amount of ImImPy in equivalent is shown on the right side of FIG. 7, in case of 7a=25 µM.

INDUSTRIAL APPLICABILITY

The invention relates to a reagent enabling selective interstrand-crosslinking of a specific nucleotide sequence existing on DNA. This potentially has a possibility of first pharmaceutical creation of drugs useful for significant gene sequences on human genome or gene abnormalities at gene level.

What is claimed is:

1. A compound capable of interstrand-crosslinking the double strands of DNA, as represented by the general formula (I):

A-L-B-X-B-L-A  (I)

wherein, is selected from the group consisting of a pyrrole optionally having one or more substituents and an imidazole optionally having one or more substituents;

A is a chemical structure having a cyclopropane ring:

L is a linker having a vinyl group; and

X is a spacer binding the component A-L-B.

2. The compound according to claim 1, wherein the spacer X binding the A-L-B component is a carbonyl group or acyl group derived from organic dicarboxylic acid.

3. The compound according to claim 2, wherein the organic dicarboxylic acid is a saturated or unsaturated aliphatic dicarboxylic acid or an aromatic dicarboxylic acid.

4. The compound according to claim 1, wherein the A-L-B component of the compound represented by the general formula (I) is a compound represented by the following formula (II):

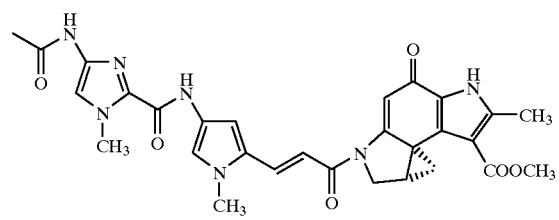
(II)

or by the following formula (III):

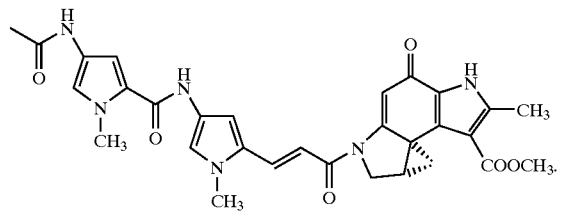
(III)

5. The compound according to claim 4, wherein the compound represented by the general formula (I) is a compound represented by the following formula (IV):

(IV)

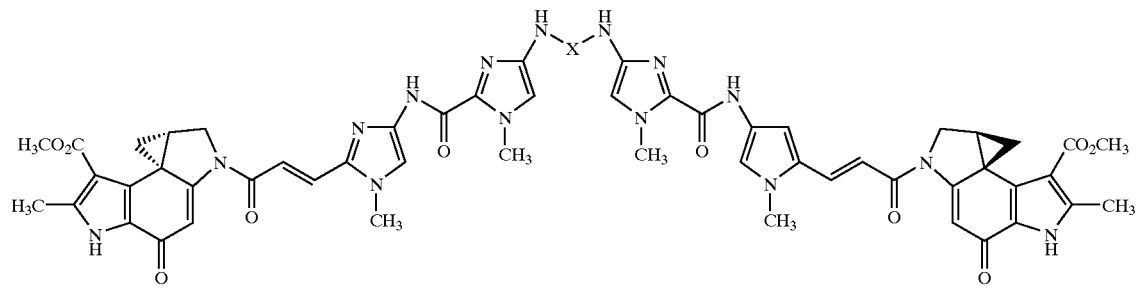

wherein, X represents a —CO— group, —CO—CH=CH—CO group, —CO—(CH$_2$)$_4$—CO— group, or —CO—(p-C$_6$H$_4$)—CO-group.

6. A method for interstrand-crosslinking a specific nucleotide sequence region of double-stranded DNA, using a compound according to claim 1.

7. The method according to claim 6, wherein the interstrand-crosslinking of double-stranded DNA is performed in the presence of a substance having a chemical structure capable of recognizing a nucleotide sequence of DNA.

8. The method according to claim 7, wherein the substance having a chemical structure capable of recognizing a nucleotide sequence of DNA is a substance represented as ImImPy.

9. The method according to claim 6, wherein the specific nucleotide sequence is TGGC or GCCA or a complementary chain thereto.

10. An interstrand-crosslinking agent of double-stranded DNA, the interstrand-crosslinking agent comprising a compound according to claim 1.

11. A pharmaceutical composition containing a compound according to claim 1 and a pharmaceutically acceptable carrier.

12. A pharmaceutical composition according to claim 11, the pharmaceutical composition being a therapeutic agent of cancer.

* * * * *